United States Patent [19]

Scanlan, Jr.

[11] 4,161,951
[45] Jul. 24, 1979

[54] NEEDLE DRIVER

[75] Inventor: Dennis R. Scanlan, Jr., Boca Raton, Fla.

[73] Assignee: Scanlan International, Inc., St. Paul, Minn.

[21] Appl. No.: 900,719

[22] Filed: Apr. 27, 1978

[51] Int. Cl.$^2$ ............................................. A61B 17/06
[52] U.S. Cl. ................................................... 128/340
[58] Field of Search ............... 128/335, 339, 340, 326, 128/334 R, 334 C; 81/5.1 R, 5.1 B; 7/102; 69/20, 45; 12/103; 112/28, 49

[56] References Cited

U.S. PATENT DOCUMENTS

| | | | |
|---|---|---|---|
| 269,408 | 12/1882 | Goodfellow | 7/102 |
| 1,037,864 | 9/1912 | Carlson et al. | 128/340 |
| 1,464,832 | 8/1923 | Richardson | 128/340 |
| 3,090,386 | 5/1963 | Curtis | 128/340 |
| 3,349,772 | 12/1967 | Rygg | 128/340 |
| 3,470,875 | 10/1969 | Johnson | 128/334 R |

OTHER PUBLICATIONS

Scanlan Instrument Catalogue, pp. 35–36.

Primary Examiner—Robert W. Michell
Assistant Examiner—C. F. Rosenbaum
Attorney, Agent, or Firm—Frederick A. Fleming

[57] ABSTRACT

A pliers-like device to facilitate certain surgical procedures, such as coaptation of the surgically split sternum, for thrusting a needle having a coaxial suture through tough tissue. The device has two elongate jaws, mechanically articulated at one end for opposable action by manual operation. The free end of the upper jaw is forked and the free end of the lower jaw has a socket to hold the needle in direction toward the fork. Features of the invention include a channel to accommodate the suture and a kerf to facilitate insertion of the suture into the socket. An optional improvement on the device provides a clamp to releasibly clamp the needle in the socket by the action of a spring-biased pin controlled by an accessory lever.

7 Claims, 5 Drawing Figures

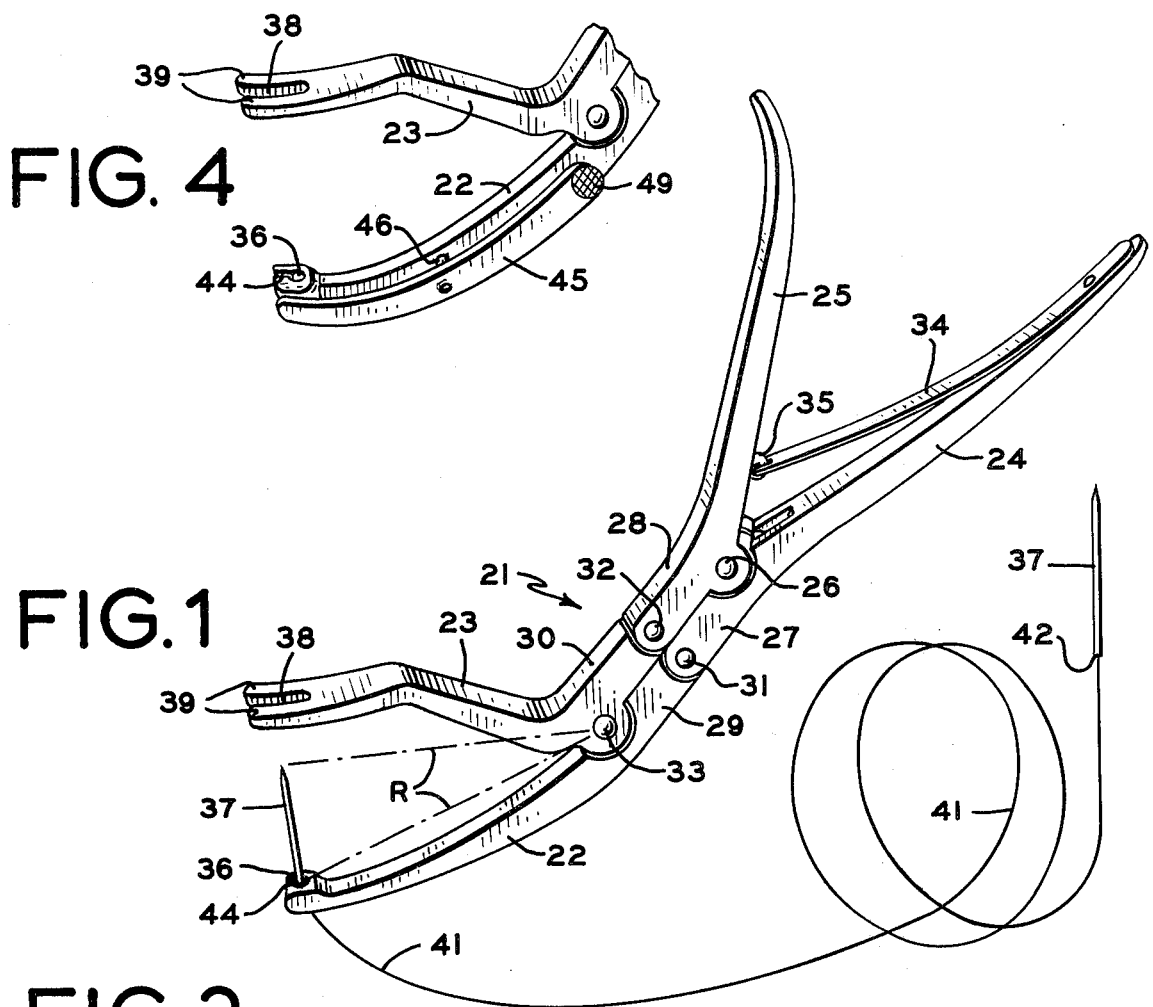

NEEDLE DRIVER

BACKGROUND OF THE INVENTION

1. Field of the Invention

My invention relates to surgery and is an instrument for bringing the edges of the surgically split sternum into coaptation; it is a device designed to hold and drive a needle having a coaxial suture through the sternum; specifically, a needle holder.

2. Description of the Prior Art

It is reasonable to believe that in the ancient art of leather-working or similar craft, there was a pliers-type device having a first jaw adapted to support a needle and a second jaw adapted to cooperate with the first jaw, to support the workpiece against the force of the needle, letting the needle penetrate the workpiece and being forked to allow the needle point to extend beyond the second jaw. As a species of the above generic invention, my invention is a needle driver adapted for driving needles of a special type used in contemporary surgery, the needle having the suture fixed within a coaxial aperture in the base of the needle, as distinguished from the obsolescent type having a suture threaded through an eye in the needle. My search of the prior art uncovered no disclosure directed to driving needles having coaxial sutures, but the following U.S. Patents disclose other species of the above generic invention:

U.S. Pat. No. 1,037,864 9/1912 Carlson et al
U.S. Pat. No. 1,464,832 8/1923 Richardson
U.S. Pat. No. 3,349,772 12/1967 Rygg The inventions of both Richardson and Rygg are aimed at providing the needle, supported in a lower jaw with an enclosure over an appreciable part of its length, to support the needle against bending, employing spring means to effect retraction of the supporting enclosure during closure of the forceps on the tissue, to allow the needle to penetrate a greater length. The invention of Carlson et al is aimed at means for engaging and receiving the point of the needle in the upper jaw after the needle passes through the tissue, to aid in completing the stitch. While each of the references discloses a pliers-type device and each has a socket for holding the needle, they are all distinguisable from my invention because they are not adapted for driving needles having coaxial sutures, for which my invention is intended: the socket-channel-kerf means disclosed here are unique to my invention.

While adaptable to other procedures, my needle driver is specifically aimed at facilitating thoracic surgery of the type in which entrance is made by midline incision and midline splitting of the sternum, to afford access to the chest cavity by lateral retraction of the two sides of the rib cage. This procedure has become commonplace in recent times, following the successful introduction of the heart-lung machine and the popularization of surgical techniques for correction of septal, valvular, and vascular defects of the heart. Closing the surgical opening after completion of such procedures, the two sides of the split sternum must be reunited by mechanical means. The usual procedure is to employ a series of eight individual sutures placed at right angles to the incision and parallel with each other. Each stitch is made by a separate suture and each suture has a needle fixed coaxially at each end, the needles being inserted from the internal surface of the sternum to its anterior surface. All of the sutures are loosely placed until completion of the last stitch, when each pair of free ends of each suture is drawn together, bringing the two edges of the split sternum together in coaptation. The two free ends of each suture are drawn taught and joined together by surgical knot, or in the case of metal sutures, by other procedures such as twisting together, the excess being snipped off.

The sternum consists of tough bony surfaces of variable thickness with a space in between filled with osseous trabeculae, the interstitial space being filled with marrow-like tissue having blood forming function. In thickness, it is not unusual to find in the human male a sternum thickness of as little as one-eighth or as great as one half-inch. The toughness of the sternum is therefore subject to considerable variability.

In some cases, it is no problem to insert the sutures through the sternum using conventional needle forceps but in the majority of cases it is a difficult job and in some cases it is not possible to do so with conventional means and an alternative technique must be employed. One such alternative is to encircle the body of the sternum with the sutures, passing the sutures through the intercostal spaces just lateral to the sternum. This procedure is believed to be inferior because it does not afford secure posterior-anterior coaptation, and because of the considerable bulk of the sutures, particularly that of the loops standing between the posterior surface of the sternum and the pericardium. Another alternative is to drill holes into the sternum and to thread the sutures into those holes. Such drilling leads to greater traumatization and hemorrhaging of the sternum tissue. Moreover, since the drilled tissue will bleed, and since the sutures are passed from the hidden interior surface of the sternum to the anterior surface, it is difficult to locate the holes for threading the sutures therein.

The problem is to provide means for conveniently and reliably inserting the sutures in the preferred way, penetrating the body of the sternum approximately midway between the surgical midline and the lateral margin of the sternum. The need for a device to facilitate this procedure has been strongly felt by the renowned surgeons in the principal cardiac surgery centers of the U.S., and it was in response to their request that I sought for a solution to the problem and made the invention disclosed herein.

SUMMARY OF THE INVENTION

My invention is a device to drive a needle through the bony structure of the sternum, to facilitate closing the chest cage after thoracic surgery. My needle driver resembles a pliers, with handles for manipulation and with jaws to drive the needle and support the sternum. My needle driver is specifically intended to drive straight needles having coaxial sutures of the type being fixedly sleeved within the tubular base of the needle. Proximate to the end of the lower jaw of my needle driver and orientated toward the upper jaw is a socket of diameter to accommodate the needle; at the base of the socket is a channel of lesser diameter to accommodate the suture. At the end of the lower jaw is a kerf, cut into the socket and aperture, for inserting the suture therein. The end of the upper jaw is forked, to provide that the tip of the needle may pass therethrough after penetrating the tissue.

Curved needles having sutures coaxial with the base of the needle are common, but while the curved needle is well adapted for use held in an ordinary forceps and applied to soft tissues, it is not suited to the application disclosed here, where the thrust force is applied to the base of the needle and the needle acts as a column for driving the point through the tissue. The use of straight needles with coaxial sutures is strange to current practice but it is practiced in my invention, although not subject to the claims.

In closing the sternum with my needle driver, prefabricated sutures of length about eighteen inches are used, the coaxial needles fixed at each end. The diameter of the needle is appreciably greater than that of the suture, there being a reduced diameter at the foot of the needle at the exit point of the suture.

At the base of the socket an annular step results from the difference in diameters of the socket and the channel. That step serves to support the foot of the needle, to transmit the force operative in the mechanical system of the driver, to drive the needle into the tissue.

The kerf is of width to accommodate the suture only, so that to load my needle driver with a needle, one must insert the suture sidewise into the kerf, then insert the foot of the needle endwise into the socket.

In practicing my invention, it is preferred that needles of circular cross section be used, and that the socket be of corresponding circular cross section, to accommodate the needle in friction fit. This fit is ordinarily all that is required to secure the needle within the socket, particularly after some experience is gained in the use of the needle driver, with attention to maintain a slight tension on the suture until the needle is placed at the point of insertion.

An alternative form of my needle driver may include accessory means for clamping the needle in the socket. My preferred form of accessory needle clamping means includes a lever-actuated, spring-biased pin which exerts a sidewise holding force on the body of the needle within the socket, the pin traveling in a race directed normal to the socket. Spring bias is simply achieved by suspending the actuating lever on the lower jaw by means of a cylindrical post of spring steel, the post serving at once as a fulcrum and as a spring.

The primary consideration in the alternative form with accessory clamping means is simplicity, to facilitate cleansing and sterilization of the instrument.

The general object of my invention is to provide the surgeon with an implement to facilitate driving a suture through tough tissue, specifically, the sternum. A specific object is to provide a needle driver for use with sutures of contemporary design having needles fixed coaxially at each end of the suture. A further object is to provide a manually operated needle driver affording mechanical advantage to multiply the power of the surgeon's hand, and to contain the operative forces local to the circuit of the implement.

The advantages of my needle driver include the following:

It affords the means for a reliable procedure for closing the chest cage. Its use avoids the need for drilling holes in the sternum or the alternative procedure of sternum encircling sutures in the difficult cases.

DESCRIPTION OF THE DRAWINGS

FIG. 1 is an over-all perspective view of the needle driver, illustrated with a needle in place in the socket of the lower jaw, the needle having a coaxial suture and a similar needle at the other end of the suture.

FIG. 2 is an enlarged midplane section of the end of the lower jaw, the section plane passing through the two jaws and the handles (not shown).

FIG. 3 is an enlarged plan view of the upper face of the end of the lower jaw.

FIG. 4 is a perspective view corresponding to FIG. 1 which shows the upper and lower jaws of an alternative form of the needle driver having a clamp.

FIG. 5 is an enlarged plan view of the upper surface of the lower jaw of the alternative form of the needle driver illustrated in FIG. 4.

DESCRIPTION OF THE PREFERRED EMBODIMENT

The needle driver 21 (FIG. 1) is a surgical implement of the pliers-type, having a socketed lower jaw 22 articulated for action in a common plane with a forked upper jaw 23 and affording a mechanical advantage by means such as the compound pivoted lever-fulcrum system illustrated in FIG. 1, which compound means is common to other familiar surgical instruments such as the rongeur of Scanlan International, Inc. As is obvious by inspection of the drawing, closing the handles 24, 25 imparts an action around the pivot 26 causing the arms 27, 28 to separate in concert with secondary arms 29, 30 at pivots 31, 32, to effect closing of jaws 22, 23 around pivot 33. While other mechanical systems which afford mechanical advantage, such as the scissors or the tweezers types, would serve the purpose of closing the jaws, I selected the compound system illustrated in FIG. 1 because it has proved satisfactory in comparable applications. Note that the jaws of the instrument are normally held open by action of the spring 34 attached to handle 24 and operating through the roller 35 on handle 25.

Proximate to the extreme end of the lower jaw 22, in its upper face opposite the forked upper jaw 23, is a cylindrical socket 36 (cf. FIGS. 2, 3) of diameter to accommodate by frictional fit the base of a needle 37 and to orientate the needle fitted therein toward the free space between the tynes 39 of the fork 38 in the upper jaw 23 (FIG. 1).

In the bottom of the socket 36 and coaxial with it is a cylindrical passage of lesser diameter, the channel 40, to accommodate the suture 41. The disparity in the diameters of the socket 36 and the channel 40 gives rise to an annular step 43 at the bottom of the socket 36. Similarly, the difference in diameters of the needle 37 and the suture 41 gives rise to the annular foot 42 at the base of the needle 37 (cf. FIG. 1, needle 37 at right-hand side of drawing). The dimensions of these elements are selected to provide secure seating for the foot 42 on the step 43, to afford a platform for thrusting the needle 37 into the tissue.

Since my needle driver is primarily intended for use with sutures having a needle at each end, like that illustrated in FIG. 1, it would be impossible to place the needle 37 in the socket 36 but for the kerf 44 (cf. FIG. 3), a slot cut into the end of the lower jaw 22 at midplane to the depth of the common axis of the socket 36 and channel 40.

The orientation of the socket 36 is in the midplane of action of the jaws 22, 23 and its direction is selected to minimize the sweep of the end of the needle 37 relative to the fork 38 during operation of the instrument. The most favorable direction is approximately that which places the base of the needle and its point at the same distance R from the pivot 33, as indicated on FIG. 1. My needle driver may be employed with needles of selected length, so that in determining the direction of the needle orientation, a needle of average length is employed.

DESCRIPTION OF THE ALTERNATIVE EMBODIMENT

An alternative form of my invention is illustrated in FIGS. 4 and 5, being substantially identical with the foregoing disclosure except that means are added for clamping the needle in position in the socket: The clamp arm 45 is mounted on the side of, subtantially parallel with and coextensive with the jaw 22 by means of a spring steel post 46. The distal end of the arm 45 carries a cylindrical pin 47, fixed to the arm at substantially a right angle and directed through a race 48 (cf. FIG. 5) in the jaw 22 toward the midpoint of the socket 36. The free end of the pin 45 extends into the socket 36 but may be retracted for inserting the needle by pressing the clamp arm 45 at the thumbhold 49, whereupon the arm 44 turns on the spring post 46 as a fulcrum. Release of pressure on the thumbhold 49 causes the pin 47 to press against the needle 37 in the socket 36, clamping it against inadvertent withdrawal. The spring post 46 is mounted in a drilled hole in side of the jaw 22 and fixed by means such as welding; the clamp arm 45 is fixed to the post 46 and the pin 47 by similar means.

I claim:

1. In a needle driver, to assist the surgeon in inserting sutures in tough tissue such as the sternum, for manipulation of sutures, particularly of the type having a straight needle at each end of the suture and in which the suture is fixed coaxially in the base of each needle and in which a disparity in diameters of the needle and the suture establishes an annular foot at the base of the needle, the combination of the following elements:
   a lower jaw, being an elongate member;
   an upper jaw, being a similar elongate member, the two jaws being articulated at one end by means affording reciprocation of the free ends of the jaws;
   a cylindrical socket proximate to the free end of the lower jaw in its upper face, to receive the base of the needle and direct the needle point toward the free space within a fork at the end of the upper jaw;
   a cylindrical channel, coaxial with the socket but of lesser diameter, extending from the bottom of the socket to the lower face of the lower jaw, to accommodate the suture fixed coaxilly in the base of the needle;
   an annular step at the bottom of the socket, arising from the difference in diameters of the socket and the channel, the annular step accommodating the annular foot at the base of the needle, serving as a platform, to impart thrust thereupon when the jaws are closed to drive the needle through tissue placed thereinbetween; and
   a kerf in the lower jaw, of width sufficient to accommodate the diameter of the suture but not that of the needle, the kerf extending to the common axis of the socket and channel, to permit loading of the needle into the socket by first sliding the suture sidewise into the kerf and then seating the needle into the socket by drawing the suture down through the channel.

2. A needle driver as in claim 1, in combination with needle clamping means to secure the needle in the socket.

3. A needle driver as in claim 2, in which the needle clamping means comprises the following combination of elements:
   a pin;
   a race, orientated in the lower jaw at substantially right angles to the socket, to accommodate the pin, permitting the end thereof to extend into the socket, to contact a needle in the socket;
   a clamp arm mounted on the side of the lower jaw by means of
   a spring post, the clamp arm being fixed to the pin and affording spring bias to urge the pin into the race against a needle therein, and
   a thumbhold, for actuating the clamp arm to release the needle.

4. A needle driver to aid the surgeon in setting sutures in tough tissue, the needle driver being specifically adapted to manipulate sutures of the type having straight needles coaxially fixed at each end of the suture, comprising the following combination of elements:
   a pliers-like device having at least one pivot, a pair of actuating handles and a pair of working jaws;
   an upper jaw with a forked end;
   a lower jaw having a socket proximate to its free end, the socket being directed to support a needle aimed at the free space of the fork of the upper jaw, the socket having at its bottom
   a channel to accommodate the suture;
   an annular step at the bottom of the socket for supporting the base of the needle; and
   a kerf proximate to the end of the lower jaw, affording passage for insertion of the suture into the socket, for loading the needle therein.

5. A needle driver for manipulating sutures of the type fixed coaxially in the end of a needle, comprising the following combination of elements;
   a hand operated, pilers-like implement having a blunt-ended lower jaw and a fork-ended upper jaw, affording reciprocating action of the blunt end of the lower jaw to the fork end of the upper jaw;
   a socket in the upper surface of the blunt end of the lower jaw, to support the base of the needle, directing the needle toward the free space in the fork;
   a channel at the bottom of the socket, to accommodate the suture;
   an annular step at the bottom of the socket, to afford a thrusting platform against the base of the needle; and
   a kerf in the blunt end of the lower jaw, to permit loading the suture into the socket.

6. A needle driver as in claim 5 having accessory clamp means to secure the needle in the socket against unintentional removal.

7. A needle driver as in claim 6 in which the clamp means is a spring-biased pin operable in a race normal to the socket.

* * * * *